US009107880B2

(12) United States Patent
Buzzi

(10) Patent No.: US 9,107,880 B2
(45) Date of Patent: Aug. 18, 2015

(54) PHARMACEUTICAL USE OF PROTEIN MOLECULES IMMUNOLOGICALLY CORRELATED TO DIPTHERIA TOXIN

(76) Inventor: Silvio Buzzi, Ravenna (IT)

(*) Notice: Subject to any disclaimer, the term of this patent is extended or adjusted under 35 U.S.C. 154(b) by 766 days.

(21) Appl. No.: 12/302,739

(22) PCT Filed: May 31, 2006

(86) PCT No.: PCT/IT2006/000409
§ 371 (c)(1),
(2), (4) Date: Apr. 9, 2009

(87) PCT Pub. No.: WO2007/138621
PCT Pub. Date: Dec. 6, 2007

(65) Prior Publication Data
US 2009/0270319 A1    Oct. 29, 2009

(51) Int. Cl.
*A61K 39/05* (2006.01)
*C07K 14/34* (2006.01)
*A61K 38/16* (2006.01)

(52) U.S. Cl.
CPC .............. *A61K 38/164* (2013.01); *A61K 39/05* (2013.01); *C07K 14/34* (2013.01)

(58) Field of Classification Search
None
See application file for complete search history.

(56) References Cited

U.S. PATENT DOCUMENTS 5,614,382 A    3/1997 Metcalf
7,358,254 B2 *  4/2008 Robl et al. .................... 514/256

FOREIGN PATENT DOCUMENTS

EP         0 616 034 A2    2/1994
WO       WO 02/055105      7/2002

OTHER PUBLICATIONS

Papini et al. FEBS letters. 215(1):73-78, May 1987.*
Alphabetical list of Specific Diseases/Disorders: http://www.mic.stacken.kth.se//Diseases/alphalist.html retrieved Aug. 22, 2011.*
Buzzi et al (Therapy (2007) 4(3), 293-298.*
Salam Al Karadaghi. Sequence alignment and amino acid sbustitution (replacement) matrices. Retrieved from http://www.proteinstructures.com/Sequence/Sequence/amino-acid-substitution.html on Mar. 6, 2012.*
Biochemistry. 5th edition. Introduction to Chapter 3. Berg JM, Tymoczko JL, Stryer L. New York: W H Freeman; 2002. Retrieved from: http://www.ncbi.nlm.nih.gov/books/NBK21177/ Mar. 6, 2012.*
Altschul et al., "Gapped BLAST and PSI-BLAST: a new generation of protein database search programs", Nucleic Acids Res., 25: 3389-3402 (1997).
Altschul et al., "Basic local alignment search tool", J. Mol. Biol., 215: 403-410 (1990).

Bartolozzi et al., I vaccini, UTET, pp. 114, 164 (2001).
Bowie et al., "Deciphering the message in protein sequences: tolerance to amino acid substitutions", Science, 247:1306-1310 (1990).
Buzzi et al., "CRM197 (non-toxic diphtheria toxin): effects on advanced cancer patients", Cancer Immunol. Immunother., 53:1041-1048 (2004).
Database Biosis [Online], Biosciences Information Service, Philadelphia, PA (2005) Gaillard Pieter et al., "Diphtheria toxin receptor-targeted brain drug delivery", pp. 185-198, XP002420282, Database accession No. PREV200510297648.
Delange et al., "Amino-acid sequence of fragment A, an enzymically active fragment from diphtheria toxin", J. Proc. Nat. Acad. Sci. USA, 73: 69-72 (1976).
Devereux et al., "A comprehensive set of sequence analysis programs for the VAX", Nucleic Acids Research 12:387-395 (1984).
Falmagne et al., "The complete amino acid sequence of diphtheria toxin fragment B. Correlation with its lipid-binding properties", Biochim. Biophys. Acta., 827: 45-50 (1985).
Giannini et al., "The amino-acid sequence of two non-toxic mutants of diphtheria toxin: CRM45 and CRM197", Nucleic Acids Research, IRL Press Ltd., Oxford, GB, 12(10):4063-4069 (1984).
Gupta et al., "Differences in the immunogenicity of native and formalinized cross reacting material (CRM197) of diphtheria toxin in mice and guinea pigs and their implications on the development and control of diphtheria vaccine based on CRMs", Vaccine, Butterworth Scientific, Guildford, GB, 15(12-13):1341-1343 (1997).
Harrison's Principles of Internal Medicine, ninth edition, pp. 672-674.
Karlin and Altschul, "Applications and statistics for multiple high-scoring segments in molecular sequences", Proc. Natl. Acad. Sci. USA, 90:5873-5877 (1993).
Karlin and Altschul, "Methods for assessing the statistical significance of molecular sequence features by using general scoring schemes", Proc. Natl. Acad. Sci. USA, 87:2264-2268 (1990).
Miyagawa et al., "Localization of heparin-binding EGF-like growth factor in the smooth muscle cells and macrophages of human atherosclerotic Plaques", J. Clin. Invest., 95: 404-411 (1995).
Papini et al., "Diphtheria Toxin and Its Mutant CRM 197 Differ in their Interaction with Lipids", FEBS Letters, 215(1):73-78 (1987).
Park et al., "The Production of Diphtheria Toxin", J. Exp. Med., 1:164-185.
Raab et al., "Heparin-binding EGF-like Growth Factor", Biochim. Biophys. Acta., 1933:179-199 (1997).
Sigma-Aldrich® with the number CAS 92092-36-9, Feb. 23, 2011.
Sigma-Aldrich® with the number MDL MFCDOOI 66638 Feb. 23, 2011.
Uchida et al., "Diphtheria toxin and related proteins", J. Biol. Chem., 248: 3838-3844 (1973).
International Search Report for PCT/IT2006/000409 dated Feb. 15, 2007.
Written Opinion for PCT/IT2006/000409 dated Feb. 15, 2007.
International Preliminary Report on Patentability for PCT/IT2006/000409 dated Dec. 3, 2008.
First Office Action in CN 200680054823.6.
Office Action dated Nov. 8, 2011 in counterpart Japanese Patent Application No. 2009-512775.

(Continued)

*Primary Examiner* — Oluwatosin Ogunbiyi
(74) *Attorney, Agent, or Firm* — Marshall, Gerstein & Borun LLP

(57) ABSTRACT

Protein molecules immunologically correlated to diphtheria toxin are proposed for the treatment of atherosclerosis and further correlated pathologies.

7 Claims, 1 Drawing Sheet

(56) References Cited

OTHER PUBLICATIONS

Mitamura et al., "Diphtheria toxin binds to the epidermal growth factor (EGF)-like domain of human heparin-binding EGF-like growth factor/diphtheria toxin receptor and inhibits specifically its mitogenic activity", The Journal of Biological Chemistry, 270(3):1015-1019 (1995).

Partial translation of Fukuoka Igaku Zasshi, 2004, vol. 95, No. 11, pp. 286-290 (right column, line 1 to the last line, p. 289).
Partial translation of therapeutic research, 1996, vol. 17, No. 3, pp. 791-799 (left column, line 5 to right column, the last line, p. 794).
Partial translation of therapeutic research, 2003, vol. 24, No. 2, pp. 142-149 (left column, line 4, p. 145 to left column, line 2, 146).

* cited by examiner

```
                        SEQUENCE LISTING

<160> NUMBER OF SEQ ID NOS: 1

<210> SEQ ID NO 1
<211> LENGTH: 535
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CRM197

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Val Glu Ser Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Val Ala Ala Leu
    290                 295                 300
```

-continued

```
Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Asn Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
                420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530                 535
```

PHARMACEUTICAL USE OF PROTEIN MOLECULES IMMUNOLOGICALLY CORRELATED TO DIPTHERIA TOXIN

TECHNICAL FIELD

The current invention relates to uses of protein molecules for the treatment of atherosclerosis and for the treatment and/or prophylaxis of further pathologies correlated to atherosclerosis.

BACKGROUND ART

Pathologies of the cardiovascular system are now one of the most prominent causes of death in medium to highly industrialized countries.

Atherosclerosis is a cardiovascular pathology characterized by hardening and narrowing of the arteries that occurs in most people when growing old. Atherosclerosis does not usually display symptoms until the flow within blood vessels has been seriously compromised. Typical symptoms of atherosclerosis include chest pain, when a coronary artery is involved, or leg pain, when a leg artery is involved. Possible complications of atherosclerosis include apoplexy, necrosis, and coronary artery disease (one symptom of which is angina) with ischemia and infarct.

On the basis of that which has been stated above, it is clear there is still a considerable need to make drugs available for the treatment of atherosclerosis and correlated pathologies.

DISCLOSURE OF INVENTION

It is an object of the present invention to provide new possibilities in the treatment of atherosclerosis and correlated pathologies.

According to the current invention, there are provided methods for the treatment of atherosclerosis and correlated pathologies and uses of diphtheria toxin derivatives in the preparation of drugs for the treatment of atherosclerosis and correlated pathologies as claimed in the independent claims that follow at the end of this description, and, preferably, in any one of the single claims directly or indirectly dependent on the independent claims.

Unless the contrary is explicitly stated, the following terms have the meaning indicated below.

In the present text "percentage of identity" and "% of identity" between two amino acid sequences means the percentage of identical amino acid residues in corresponding positions in the two sequences in optimum alignment.

To determine the "percentage of identity" of the two amino acid sequences or of nucleic acids, the sequences are mutually aligned to reach an optimum comparison. Gaps (that is, cancellations or insertions) can be introduced into the sequence. The amino acids in corresponding positions are then compared. When a position in the first sequence is occupied by the same amino acid that occupies the corresponding position in the second sequence, the molecules are identical in that position (that is, the position is identical). The percentage of identity between the two sequences is the result of the number of identical positions shared by the sequences [that is the percentage of identity=(number of identical positions/total number of positions)×100]. According to a preferred embodiment, the sequences are of the same length.

The compared sequences may present gaps.

The percentage of identity can be obtained by means of mathematical algorithms. A non restrictive example of a mathematical algorithm used for the comparison of two sequences is the algorithm of Karlin and Altschul [(1990), Proc. Natl Acad Sci USA 87: 2264-2268] modified by Karli and Altschul [(1993). Proc. Natl Acad Sci USA 90: 5873-5877]. Such an algorithm is incorporated in Altschul's BLASTn and BLASTp programs [Altschul, et al, (1990). J Mol Biol 215: 403-410].

To obtain alignments also in the presence of one or more gaps it is possible to use methods that assign a relatively high penalty to each gap and a lower penalty to each additional amino acid residue or nucleotide in the gap (such additional amino acid residue or nucleotide is defined as an extension to the gap). Obviously, high penalties will determine optimized alignments with a smaller number of gaps.

An example of a program suitable for the realization of this type of alignment is the BLAST program that Altschul et al. described [(1997). Nucleic Acids Res 25: 3389-3402]. To this end, the BLASTn e BLASTp programs can be used with the default parameters. The matrix BLOSUM62 is usually adopted when using the BLAST program.

A preferred and non restrictive example of a program for obtaining an optimum alignment is GCG Winsconsin Bestfit package [University of Winsconsin, USA; Devereux et al. (1984). Nucleic Acids Research 12:387]. Also in this case default parameters are used, that for a sequence of amino acids foresee a penalty of −12 for a gap and a penalty of −4 for each extension.

In the current text by "homologous positions" is meant positions that have two homologous amino acids, that is amino acids endowed with similar physicochemical properties. For example, amino acids belonging to the same groups such as: aromatic (Phe, Trp, Tyr), acid (Glu, Asp), polar (Gln, Asn), basic (Lys, Arg, His), aliphatic (Ala, Leu, Ile, Val), with one hydroxy group (Ser, Thr), with short lateral chain (Gly, Ala, Ser, Thr, Met). One would expect that replacements between such homologous amino acids would not change the phenotype of the protein (preservative replacement of amino acids). Specific examples of preservative replacement are well known in this technical field and are described in various works [e.g., Bowie et al. (1990). Science 247:1306-1310].

In the current text by "stringent conditions" is meant, preferably, a washing of one hour with buffer SSC (0.15 M sodium chloride solution and 20 mM sodium citrate) and 0.1% SDS (sodium dodecil sulphate) at 50° C. Alternatively, "stringent conditions" have been described in the past [Ausubel F M et al. eds. (1989) Current Protocols in Molecular Biology, Vol. I, Green Publishing Associates, Inc. and John Wiley & Sons Inc. New York].

In the current text by "pharmaceutically acceptable derivative" is meant a salt or a complex (i.e. a compound in which one or more molecules or ions form one or more coordinate bonds to one or more metal atoms or metal ions) that maintains the biological properties of the original molecule. Non limiting examples of methodologies for the preparation of such derivatives include the following items: addition of inorganic acids (for example, hydrochloric acid, hydrobromic acid, sulfuric acid, phosphoric acid or the like) or of organic acids (for example, acetic acid, oxalic acid, maleic acid, metasulfonic acid, salicylic acid, succinic acid, citric acid or the like) to the free base of the original molecule; replacement of a proton acid of the original molecule with a metallic cation (for example, a cation of an alkaline metal or of an aluminum or the like); transfer of a proton acid of the original compound to an organic base (for example, dimethylamine, triethylamine, and the like) and coordination with such an organic base. The molecules that are the subject of the current invention are to be understood, unless the contrary is specified, as comprising their "pharmaceutically acceptable derivatives".

BRIEF DESCRIPTION OF THE DRAWINGS

Non-limiting embodiments of the present invention will be described by way of examples with reference to the accompanying figures, in which.

BEST MODE FOR CARRYING OUT THE INVENTION

Figure 1:
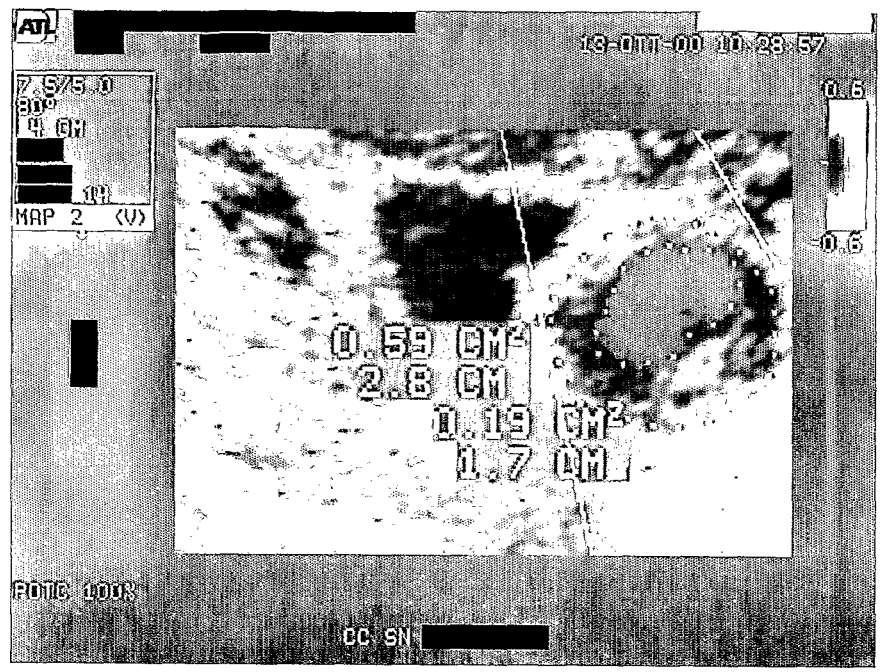
FIGS. 1 and 2 show color Doppler images carried out on the patient of example 3 before and, respectively, after the treatment with CRM197.

In accordance with a first aspect of the present invention, a protein molecule for the treatment of atherosclerosis and/or for the treatment or the prophylaxis of pathologies correlated to atherosclerosis in mammals and a use of a protein molecule for the treatment of atherosclerosis and/or for the treatment or the prophylaxis of pathologies correlated to atherosclerosis in mammals is provided. In particular, in accordance with a further aspect of the current invention, a use of a protein molecule for the production of a pharmaceutical preparation for the treatment of atherosclerosis and/or for the treatment or the prophylaxis of pathologies correlated to atherosclerosis in mammals is provided.

The pathologies correlated to atherosclerosis comprise: apoplexy, necrosis and coronary artery disease with ischemia and infarct. Ischemia can also be, in particular, renal, pulmonary, and cerebrovascular.

The protein molecule has, preferably, an identity of at least 90% with the sequence of CRM197, comprises a first and a second disulfide bridge, two fragments, both of which are connected to each other by means of the first disulfide bridge, and has a glutamic acid in position 52.

CRM197 is a toxin produced by a mutant strain of *Corynebacterium diphtheriae* [Uchida T, Pappenheimer A M Jr, Greany R (1973). Diphtheria toxin and related proteins. I. Isolation and properties of mutant proteins serologically related to diphtheria toxin. J Biol Chem 248: 3838-3844], is essentially non toxic (see Uchida et al. above), is currently used as a carrier for infantile vaccines (see, in particular, Bartolozzi G, Rappuoli R. I vaccini, UTET, 2001. pp 114, 164), differs from diphtheria toxin in the presence of a glutamic acid instead of a glycine in position 52, and is traded (for laboratory use) by Sigma-Aldrich with the number CAS 92092-36-9 and number MDL MFCD00166638. The diphtheria toxin is a toxin, as is well known, produced by *Corynebacterium diphtheriae*. The sequence and the structure of the diphtheria protein have been described [Delange R J, Drazin R E, and Collier R J (1976). Amino-acid sequence of fragment A, an enzimatically active fragment from diphtheria toxin. Proc Nat Acad Sci USA 73: 69-72, and; Falmagne P, Capiau C, Lambotte P et al. (1985). The complete amino acid sequence of diphtheria toxin fragment B. Correlation with its lipid-binding properties. Biochim Biophys Acta 827: 45-50]. CRM197 can be produced by the same methodology described by Park H W and Williams A W [J Exp Med 1:164-185] using the mutant strain of *Corynebacterium diphtheriae* previously cited (See Uchida et al. above).

According to increasingly preferred embodiments, the protein molecule should have at least 92%, 94%, 95%, 96%, 97%, 98%, 99% and 100% of identity with the sequence of CRM197. Where the protein molecule and CRM 197 show one or more different positions, preferably, at least one of these different positions should be homologous; more preferably, the different positions should be homologous.

Preferably, the protein molecule comprises a first cystein in position 186 and a second cystein in position 201. The first and the second cysteins are joined together by the first disulfide bridge. The protein molecule comprises a third cystein in position 461 and a fourth cystein in position 471. The third and fourth cysteins are joined together by means of the second disulfide bridge.

The protein molecule acts by attaching itself to HB-EGF [Raab G, Klagsbrun H (1997). Heparin-binding EGF-like Growth Factor, Biochim Biophys Acta 1933: 179-199] and stimulating the immunological system in such a way as to attract antibodies and white blood cells (Harrison's Principles of Internal Medicine, ninth edition, pp 672-674). HB-EGF is a heparin-binding growth factor that is able to activate two subtypes (HER1 and HER4) of EGFR (Epidermal Growth Factor Receptor) and is generally overexpressed in some pathological processes such as atherosclerosis [Miyagawa J I, Higashiyama S, Kawata S, et al. (1995). Localization of heparin-binding EGF-like growth factor in the smooth muscle cells and macrophages of human atherosclerotic plaques. J Clin Invest 95: 404-411].

Preferably, therefore, the molecule is able to attach itself to HB-EGF in stringent conditions and to stimulate an immunological reaction in such a way as to attract antibodies and/or white blood cells.

According to a further aspect of the current invention, a pharmaceutical preparation containing a protein molecule as defined above, or one of its pharmaceutically acceptable derivatives and an excipient and/or a pharmaceutically acceptable diluent, is provided.

According to a further aspect of the current invention, a method for the treatment of atherosclerosis and/or the treatment or the prophylaxis of pathologies correlated to atherosclerosis in mammals is provided. The method foresees the administration of an effective dose of the protein molecule, as defined above, to mammals.

Preferably, the protein molecule is administered by a hypodermic injection. In this way the risk of immediate immunological reaction in hypersensitive subjects is extremely reduced.

According to preferred embodiments, the method comprises a first phase of administration, in which a dose of the molecule is administered to the patient every first defined period. The first defined period is between two and four days. Preferably, the first defined period is of approximately three days. The duration of the first phase of administration is between ten and thirty days. Preferably, the duration of the first phase should be of approximately eighteen days.

Preferably, the method comprises a second phase of administration, which is subsequent to the first phase of administration. In the second phase a dose of the molecule is administered once every second defined period. The second defined period is between one and three months. More preferably, the second defined period is of approximately two months. The duration of the second phase is between four and eight months. More preferably, the duration of the second phase should be of approximately eight months.

Preferably, each single dose is between 0.5 and 4.0 mg, more preferably, between 0.5 and 3.6, even more preferably between 0.5 and 3.0 mg.

Preferably, the method comprises a pretreatment phase preceding the first phase of administration with the aim of identifying the patients presenting hypersensitivity of immediate type (ITH) or hypersensitivity of delayed type (DTH). The phase of pretreatment has been previously described in details [Buzzi S, Rubboli D, Buzzi G, et al. (2004). CRM197 (non-toxic diphtheria toxin): effects on advanced cancer patients. Cancer Immunol Immunother 53:1041-1048]. An ITH condition is revealed when a pruriginous and erythematous reaction develops in the injection sites within a few minutes from the protein administration, and when the level of IgE is above 500 ng/mL.

A DTH condition is revealed when a pruriginous and erythematous reaction develops in the injection sites within 24 hours from the protein administration.

Full reference is made herein to the content of the references (articles, textbooks, etc.) cited above for the purpose of a full disclosure.

Further characteristics of the current invention will be apparent from the descriptions that follow of some merely illustrative and non-limiting examples.

In particular, the examples that follow illustrate how the use of the above defined protein molecule surprisingly causes extremely relevant reduction of atherosclerotic plaques and, therefore, improvement of correlated pathologies. The following examples also show that the above defined protein molecule has extremely low toxicity (as already shown by Uchida et al. above).

Example 1

CRM197 was diluted until a concentration of 3.0 mg/mL was reached in a sterilized phosphate buffer (10-mM sodium phosphate buffer, pH 7.2) containing 10% sucrose as stabilizer. The final product was aliquoted in pyrogen-free vials and stored at −20° C.

Example 2

A 68-year-old man, with 55% stenosis (ultrasonografic examination) of the right internal carotid, was treated with a dose of 3.5 mg of CRM197, formulated as described in example 1 and given on alternate days, for six times. A further dose, like the first ones, was administered to the patient every two months, for six months. Eighteen months later an ultrasound color Doppler evidenced 27% reduction of the initial stenosis (all the cases of carotid stenosis cited in this description were detected and monitored by an ultrasound instrument always used by the same physician).

Example 3

A 74-year-old man with 40% stenosis (NASCET) of the right internal carotid (mixed plaque) and 67.8% stenosis of the common left carotid (soft plaque) was treated with a dose of 3.5 mg of CRM197, formulated as described in example 1 and given on alternate days, for six times (the left internal carotid and the right common carotid showed only a thickening of the intima). A further dose, like the first ones, was administered to the patient every two months, for six times. The patient showed a humoral immunity and a moderate delayed hypersensitivity towards diphtheria toxin and CRM197. Following the treatment the only side effect displayed by the patient was the development of a pruriginous erythema in the injection sites.

After the treatment, the patient was checked at regular intervals for a period of 58 months. After 14 months from the beginning of the treatment 8% reduction of the stenosis of the left common carotid was observed. After 25 months from the beginning of the treatment 15% reduction of the stenosis of the left common carotid was observed. After 58 months from the beginning of the treatment 71.5% reduction of the stenosis of the right internal carotid and 93.3% reduction of the stenosis of the left common carotid were observed.

FIG. 1 relates to the ultrasonography of the left common carotid carried out prior to the treatment. This ultrasonography allowed to determine a total area of the arterial section of 0.59 cm$^2$, a circumference of the entire section of 2.8 cm, a clear blood flow area (lumen) of 0.19 cm$^2$, a percentage of clear area (lumen) of 32.2%, and a percentage of the area of stenosis of 67.8%.

Figure 2:
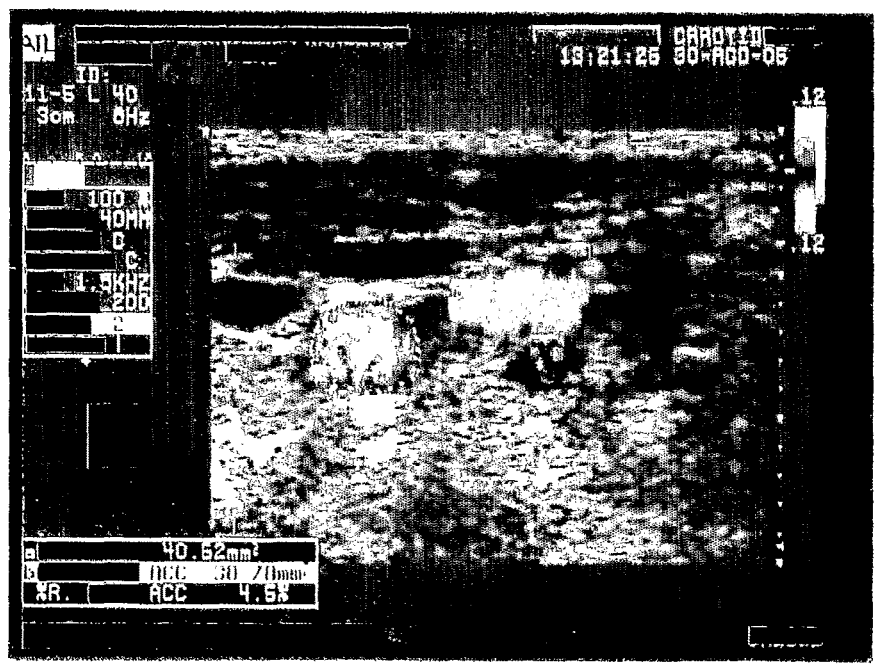

FIG. 2 relates to the ultrasonography of the left common carotid carried out 58 months after the treatment. This ultrasonography allowed to determine a total area of the arterial section of 40.62 mm$^2$, a clear blood flow area (lumen) of 38.68 mm$^2$, a percentage of clear area (lumen) of 95.5% and a percentage of the area of stenosis of 4.5%.

Example 4

A 74-year-old woman with 65% stenosis (NASCET) of the right internal carotid (mixed plaques) and 40% stenosis (NASCET) of the left internal one (mixed plaques) was treated with a dose of 1.7 mg of CRM197, formulated as described in example 1 and given on alternate days, for six times. A further dose, like the first ones, was administered every two months, for six months.

The patient showed no immunocompetence towards diphtheria toxin and CRM197.

After eight months from the beginning of the treatment 46% reduction in the stenosis of the right internal carotid and 50% in that of the left internal one were observed.

Example 5

A 79-year-old man with 59% stenosis (NASCET) of the right internal carotid and 20% stenosis (NASCET) of the left internal one (soft plaque and hard plaque, respectively) was treated with a dose of 1.7 mg of CRM197, formulated as described in example 1 and given on alternate days, for six times. A further dose, like the first ones, was administered to the patient every two months, for six months.

The patient did not show any immunocompetence towards diphtheria toxin and CRM197.

After eight months from the beginning of the treatment 90% reduction of the stenosis of the right internal carotid and 30% reduction of the stenosis of the left internal one were observed.

Example 6

A 65-year-old woman with 60% stenosis (NASCET) of the right internal carotid and 55% stenosis (NASCET) of the left internal one (mixed plaques) was treated with a dose of 1.7 mg of CRM197, formulated as described in example 1 and given on alternate days, for six times. A further dose, like the first ones, was administered to the patient every two months, for six months.

The patient did not show any immunocompetence towards diphtheria toxin and CRM197.

After sixty months from the beginning of the treatment 30% reduction of the stenosis of the internal right carotid and 25% reduction of the stenosis of the left internal carotid were observed.

Example 7

A 78-year-old woman with 60% stenosis (NASCET) of the right internal carotid and 40% stenosis (NASCET) of the left internal one (mixed plaques) was treated with a dose of 3.5 mg of CRM197, formulated as described in example 1 and given on alternate days, for six times. A further dose, like the first ones, was administered to the patient every two months, for six months.

The patient showed a strong humoral immunity towards diphtheria toxin and CRM197.

After sixty months from the beginning of the treatment 40% reduction in the stenosis of the internal right carotid and 30% reduction in that of the left internal one were observed.

The invention claimed is:

1. A method of treatment for carotid stenosis in a mammal, the method comprising the administration of an effective dose of a protein molecule to the mammal, wherein the protein molecule comprises the sequence set out in SEQ ID NO: 1 and whereby carotid stenosis is reduced in the mammal.

2. The method of claim 1, wherein the protein molecule is administered by hypodermic injection.

3. The method of claim 1, the method further comprising a first phase of administration wherein a dose of the protein molecule is administered to the mammal every first defined period for duration of ten to thirty days; the first defined period being two to four days.

4. The method of claim 3, wherein the duration of the first phase of administration is of approximately eighteen days.

5. The method of claim 3, and comprising a second phase of administration wherein a dose of the molecule is administered once every second defined period; the second defined period being of one to three months; the duration of the second phase of administration being of four to eight months.

6. The method of claim 3, wherein the dose is of 0.5 to 4.0 mg of said protein molecule.

7. The method of claim 6, wherein the dose is of 0.5 to 3.0 mg of said protein molecule.

* * * * *

UNITED STATES PATENT AND TRADEMARK OFFICE
CERTIFICATE OF CORRECTION

| | | |
|---|---|---|
| PATENT NO. | : 9,107,880 B2 | Page 1 of 1 |
| APPLICATION NO. | : 12/302739 | |
| DATED | : August 18, 2015 | |
| INVENTOR(S) | : Silvio Buzzi | |

It is certified that error appears in the above-identified patent and that said Letters Patent is hereby corrected as shown below:

On the Title Page, at Item (54), and in the Specification, column 1, line 3, "DIPTHERIA" should be -- DIPHTHERIA --.

Signed and Sealed this
Twenty-second Day of March, 2016

Michelle K. Lee
*Director of the United States Patent and Trademark Office*